United States Patent
Smolko-Schvarzmayr et al.

(10) Patent No.: US 10,100,146 B2
(45) Date of Patent: Oct. 16, 2018

(54) POLYESTER POLYQUATERNARY AMMONIUM COMPOUND COLLECTORS FOR REVERSE FROTH FLOTATION OF SILICATES FROM NONSULFIDIC ORES

(71) Applicant: Akzo Nobel Chemicals International B.V., Arnhem (NL)

(72) Inventors: Natalija Smolko-Schvarzmayr, Hjälteby (SE); Anders Klingberg, Henån (SE)

(73) Assignee: AKZO NOBEL CHEMICALS INTERNATIONAL, B.V., Arnhem (NL)

( * ) Notice: Subject to any disclaimer, the term of this patent is extended or adjusted under 35 U.S.C. 154(b) by 74 days.

(21) Appl. No.: 15/101,300

(22) PCT Filed: Dec. 15, 2014

(86) PCT No.: PCT/EP2014/077669
§ 371 (c)(1),
(2) Date: Jun. 2, 2016

(87) PCT Pub. No.: WO2015/091308
PCT Pub. Date: Jun. 25, 2015

(65) Prior Publication Data
US 2016/0304663 A1 Oct. 20, 2016

(30) Foreign Application Priority Data

Dec. 18, 2013 (EP) .................................... 13198074
Dec. 18, 2013 (EP) .................................... 13198086

(51) Int. Cl.
*B03D 1/02* (2006.01)
*C08G 63/91* (2006.01)
(Continued)

(52) U.S. Cl.
CPC ............ *C08G 63/916* (2013.01); *B03D 1/011* (2013.01); *B03D 1/016* (2013.01); *B03D 1/02* (2013.01);
(Continued)

(58) Field of Classification Search
CPC ................ B03D 1/011; B03D 2201/02; B03D 2203/06; B03D 2201/06; B03D 1/02; B03D 1/016; B03D 1/021; C08G 63/916; C07D 219/06; C07C 229/24; C07C 229/26
USPC ......................................................... 209/166
See application file for complete search history.

(56) References Cited

U.S. PATENT DOCUMENTS

2003/0013627 A1  1/2003 Bermejo Oses et al.
2010/0047194 A1* 2/2010 Bevinakatti .............. A61K 8/85
                                                                   424/59

FOREIGN PATENT DOCUMENTS

EP          0770595 A1    5/1997
EP          0980352 A1   11/1998
(Continued)

OTHER PUBLICATIONS

European Search Report for EP 13198074.0, dated May 26, 2014.
(Continued)

*Primary Examiner* — Thomas M Lithgow
(74) *Attorney, Agent, or Firm* — Matthew J. DeRuyter

(57) ABSTRACT

The present invention relates to a compound obtainable by the condensation of a polyol having 3-4 hydroxyl groups, adicarboxylic acid or a derivative thereof, an alkanolamine and a fatty acid, followed by reaction with an alkylating agent. This compound is useful as a collector in a process for the reverse froth flotation of non-sulfidic ores containing silicate as impurities, especially phosphate ores.

9 Claims, 1 Drawing Sheet

(51) Int. Cl.
  *B03D 1/016* (2006.01)
  *C07D 219/06* (2006.01)
  *B03D 1/01* (2006.01)
  *C07C 229/24* (2006.01)
  *C07C 229/26* (2006.01)

(52) U.S. Cl.
  CPC ............ *B03D 1/021* (2013.01); *C07C 229/24* (2013.01); *C07C 229/26* (2013.01); *C07D 219/06* (2013.01); *B03D 2201/02* (2013.01); *B03D 2201/06* (2013.01); *B03D 2203/06* (2013.01)

(56) References Cited

FOREIGN PATENT DOCUMENTS

| | | |
|---|---|---|
| EP | 1136471 A1 | 9/2001 |
| EP | 1949963 A1 | 7/2008 |
| WO | 2011/147855 A2 | 12/2011 |
| WO | 2012/000895 A2 | 1/2012 |
| WO | 2012/028542 A1 | 3/2012 |
| WO | 2012/089649 | 7/2012 |

OTHER PUBLICATIONS

International Search Report and Written Opinion for PCT/EP2014/077669, dated Feb. 19, 2015.
Database CA [Online], Chemical Abstracts Service, Columbus, OH, USA, Metlyakova, I.R. et al., Synthesis of Triethanolamine Adipate Oligoesters, XP272417, retrieved from STN, Database accession No. 1977:552776 abstract & Metlyakova, I.R. et al., Synthesis of triethanolamine adipate oligoesters, Sintex I Fiziko-Khimiya Polimerov, 20, 87-90 Coden: SFKPAO, ISSN 5083-4317, 1977.

\* cited by examiner

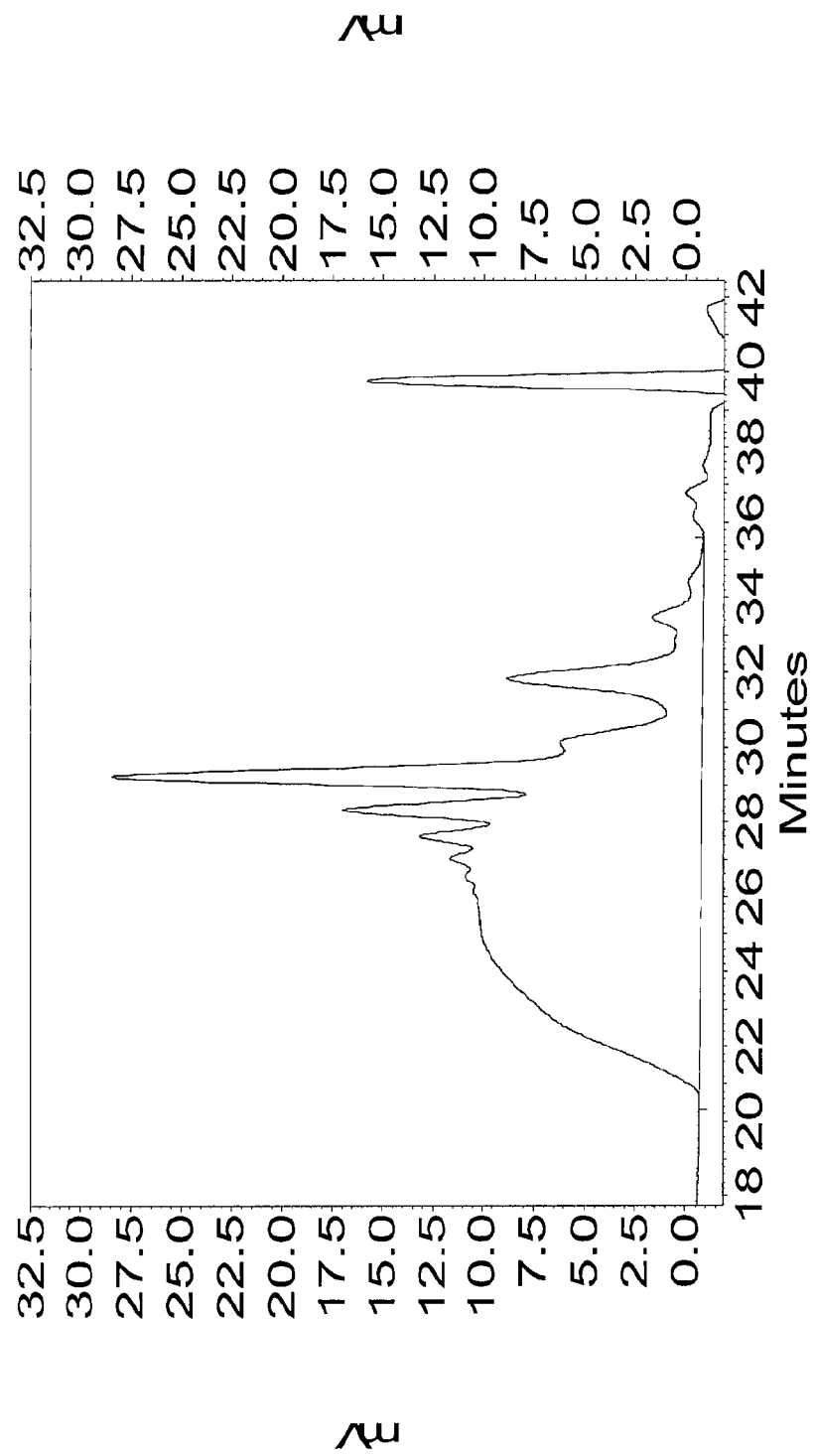

POLYESTER POLYQUATERNARY AMMONIUM COMPOUND COLLECTORS FOR REVERSE FROTH FLOTATION OF SILICATES FROM NONSULFIDIC ORES

This application is a national stage filing under 35 U.S.C. § 371 of PCT/EP2014/077669, filed Dec. 15, 2014, which claims priority to European Patent Application No. 13198074.0, filed Dec. 18, 2013 and European Patent Application No. 13198086.4, filed Dec. 18, 2013, the contents of which are each incorporated herein by reference in their entireties.

TECHNICAL FIELD OF INVENTION

The present invention relates to new polyester polyquaternary ammonium compounds which can be used in a variety of applications, e.g. as corrosion inhibitors, textile conditioners, ingredients in products of personal care, and as collectors for mineral processing. The new compound is obtainable by reacting alkanolamines with a mixture of polyalcohols, monocarboxylic acids and dicarboxylic acids followed by quaternising the resulting esters in a known manner.

TECHNICAL BACKGROUND OF THE INVENTION

During the last decade polyester polyquaternary ammonium compounds became very attractive for a variety of applications due to their good performance and excellent environmental characteristics.

EP 0 980 352 B1 relates to compounds obtained by the reaction of triethanolamine with fatty acids and dicarboxylic acids, and/or the corresponding quaternised compounds thereof, and also to textile-softening compositions containing these compounds.

In WO 2012/028542, WO 2012/089649 and WO 2011/000895 a number of different polyester polyquaternary ammonium compounds have been described for use within the field of corrosion inhibitors.

EP 1 136 471 A1 relates to products based on the esterification of alkanolamines, optionally alkoxylated, dicarboxylic acids and fatty alcohols, optionally alkoxylated, and esterquats obtainable therefrom. The products are usable in treatments for softening and conditioning of textiles, paper and hair.

EP 0 770 595 A1 relates to esterquats obtained by reacting trialkanolamine with a mixture of fatty acids, dicarboxylic acids and sorbitol, optionally ethoxylating the ester, and quaternising the product. These esterquats are used in the preparation of surface active agents, especially for hair and personal care.

WO 2011/147855 describes the process of floating calcium carbonate containing silicates as impurity, using as collectors ester quaternary compounds, which are obtainable by the condensation of a fatty alcohol, optionally alkoxylated, a fatty acid alkanolamide, optionally alkoxylated, or an alkoxylated secondary amine, a dicarboxylic acid or a derivative thereof and an alkanolamine, where the condensation product has been quaternised by a suitable alkylating agent.

EP 1 949 963 B1 relates to the flotation of non-sulfidic minerals and ores where polymeric esterquats, obtained by reacting alkanolamines, fatty acids and dicarboxylic acids and quaternising the resulting esters, are used as collectors.

However there is still a need for a broader variety of new environmentally friendly polyester polyquaternary ammonium compounds, based on renewable raw materials and easily manufactured.

SUMMARY OF THE INVENTION

It is an object of the present invention to provide environmentally friendly polyester polyquaternary ammonium compounds, which are based on renewable raw materials and which are easily manufactured, and where said compounds have improved properties in a number of applications.

It was surprisingly found that a polyester polyquaternary ammonium compound obtainable by a process including the followings steps:
1) reaction of a mixture comprising at least one alkanolamine, at least one monocarboxylic acid, at least one dicarboxylic acid and at least one polyol having 3-4 hydroxyl groups, to form a polyester, and
2) quaternization of the resulting polyester by a suitable alkylating agent; at least partly fulfills the above needs.

Surprisingly, we have found that when floating non-sulfidic ores containing silicates as impurity, a very high yield and a high selectivity (low content of acid-insoluble matter) can be achieved if the reverse froth flotation process comprises the use of the above-mentioned polyester polyquaternary ammonium compounds, obtainable by the condensation of a polyol having 3-4 hydroxyl groups, preferably glycerol, a dicarboxylic acid or a derivative thereof, a fatty acid, and an alkanolamine, and where the condensation product has been quaternised by a suitable alkylating agent.

BRIEF DESCRIPTION OF THE DRAWINGS

FIG. 1 is the SEC chromatogram from Example 1.

DETAILED DESCRIPTION OF THE INVENTION

A first aspect of the invention relates to specific polymers obtainable from the condensation of at least one polyol having 3-4 hydroxyl groups, preferably glycerol, optionally alkoxylated, and at least one alkanolamine, optionally alkoxylated, with at least one dicarboxylic acid and at least one fatty acid, followed by quaternisation of the product obtained by the condensation, and in a second aspect the present invention relates to a method for obtaining these polymers.

A third aspect of the present invention relates to the use of the aforementioned products as flotation collectors, especially for the reverse froth flotation of non-sulfidic ores containing silicates as impurities, such as ores containing calcite, phosphate or ferruginous minerals, and in particular for the reverse froth flotation of apatite.

A fourth aspect relates to a method for the reverse froth flotation of apatite in the presence of these products.

The polyester polyquaternary ammonium compound containing a polyol having 3-4 hydroxyl groups as a building block according to the present invention is a new compound.

The present invention thus relates to the manufacturing process of the new polyester polyquaternary ammonium compound and the use of the product, as well as the product itself, where the product is obtainable by the condensation of at least one polyol having 3-4 hydroxyl groups or the alkoxylated product thereof having the formula

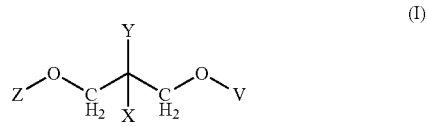

(I)

where Z=—(CH$_2$CH(CH$_3$)O)$_{m1}$(CH$_2$CH$_2$O)$_o$(CH$_2$CH(CH$_3$)O)$_{m2}$T, where T is H, m1 and m2 is independently a number 0-4, preferably m1 and/or m2 is 0, and o is 0 or a number from 1, preferably from 2, to 10, preferably to 5; preferably the sum of all o is 0; Y=—CH$_2$OZ, —CH$_2$CH$_3$ or —OZ; X=H or CH$_2$OZ; and V=Z or

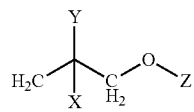

at least one dicarboxylic acid or a derivative thereof having the formula (IIa) or (IIb)

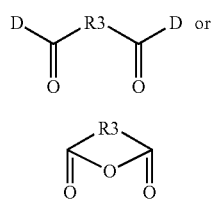

where D is —OH, —Cl, or —OR$^4$, where R$^4$ is a C1-C4 alkyl group; R3 is a bond, an alkylene radical of formula —(CH$_2$)$_z$—, in which z is an integer from 1 to 10, preferably from 2 to 4, and most preferably 2, and in which the alkylene radical may be substituted by 1 or 2 —OH groups; the group —CH=CH—, a cycloalkylene, a cycloalkenylene, or an arylene group;

at least one alkanolamine having the formula (III)

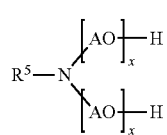

wherein each x independently is a number between 1 and 5, and the sum of all x on average is a number between 2 and 10, AO is an alkyleneoxy group having 2-4 carbon atoms, R$^5$ is a C1-C4, preferably C1-C3 alkyl group, and most preferably a methyl group, or the group [AO]$_x$H; and at least one fatty acid having the formula

R(C=O)OH                                               (IV)

where R is a hydrocarbyl group having from 7 to 23, preferably 11 to 21, carbon atoms, optionally substituted; followed by reaction with an alkylating agent, suitably a C1-C4 alkyl halide, preferably methyl chloride, or dimethyl sulphate; as a collector in a reverse froth flotation process for non-sulfidic ores containing silicate as impurities.

Neither any alcohol having the general formula R$^1$OH, where R$^1$ is a C$_2$-C$_{22}$ alkyl or alkenyl group, nor any alkoxylate thereof, is present in the reaction mixture during the condensation reaction.

In one embodiment the polyol is a compound of formula (I), where Y is —O(CH$_2$CH(CH$_3$)O)$_{m1}$(CH$_2$CH$_2$O)$_o$(CH$_2$CH(CH$_3$)O)$_{m2}$T, X is H, T is H, and V and Z are both —(CH$_2$CH(CH$_3$)O)$_{m1}$(CH$_2$CH$_2$O)$_o$(CH$_2$CH(CH$_3$)O)$_{m2}$T. This polyol is glycerol or alkoxylated glycerol. The values of m1, m2 and o are the same as above, and preferably they are all 0.

For the embodiment above where m1, m2 and o are all 0, and where the alkanolamine of formula (III) is methyl diethanolamine and the quaternisation has been performed with methyl chloride, the polymer may for example have the formula

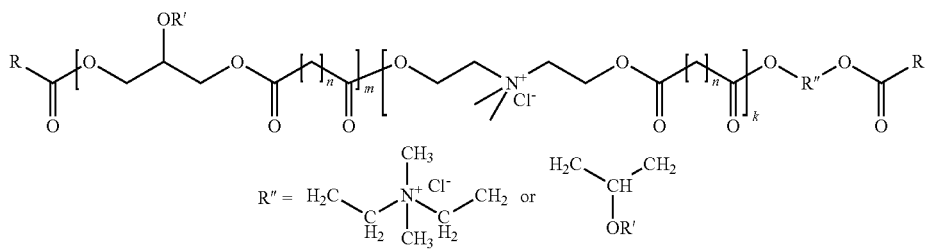

where R is a hydrocarbyl group having from 7 to 23, preferably 11 to 21, carbon atoms, optionally substituted; and R' is H or R(C=O); and n is an integer 0-10. The average value of k and m will depend on the molar ratios of the appropriate compounds (I), (IIa) or (IIb), (III) and (IV) in the reaction mixture, as well as on the reaction conditions, the m values suitably ranging between 1 and 3, and the k values suitably ranging between 2 and 7.

The formula above shows one block containing esterified glycerol and diacid, and one block containing esterified alkanolamine and diacid. The "block units" consisting of one glycerol esterified with one diacid may of course be distributed randomly with the "block units" consisting of one alkanolamine esterified with one diacid. The fatty acids either have been esterfied with a primary OH group of a glycerol unit or of an alkanolamine unit, and thus appear at the end of the chains, or have been esterified with a secondary hydroxyl group of one or several of the glycerol units. Thus, there will be hydrophobic groups distributed along the chain as well as at the ends of the chain.

Since there are at least 4 different kinds of monomeric units originating from compounds I, II, III and IV, any attempt to describe the product of the invention with a written molecular formula must of necessity only result in some kind of mean molecule, based on the amounts of the starting materials. The actual product will consist of a large number of different molecules. Even the molecules with the same kinds of units could have the units connected in different order, and contain different amounts of them. Thus the formula above should only be regarded as an example of how the units may be connected, and the product is better described by the process to make it, as described in the manufacturing process above.

A suitable method for the preparation of the polyester polyquaternary ammonium compounds subject of the present invention comprises the steps of mixing a compound of formula (I) as defined above with a compound of formula (IIa) or (IIb) as defined above, a compound of formula (III) as defined above, and a part of a compound of formula (IV), effecting an esterification condensation reaction between the compounds in the mixture, adding the rest of compound of formula (IV) and go on esterifying the product in the reaction mixture, adding an alkylating agent to the condensation reaction product and effecting a quaternisation reaction of the condensation product.

The esterification condensation reactions taking place between the compounds (I), (IIa) or (IIb), (III) and (IV) are well-known per se in the art. The reactions may be performed with an esterification catalyst, such as a Brönstedt or Lewis acid, for example methanesulfonic acid, p-toluenesulfonic acid, citric acid or $BF_3$, or without any catalyst. When a dicarboxylic acid derivative of formula (IIa) is used, wherein D is O—$R^4$, the reaction is a transesterification, which alternatively could be performed in the presence of an alkaline catalyst. Also other conventional techniques known by the person skilled in the art could be used starting from other derivatives of the dicarboxylic acids, such as from their anhydrides or their acid chlorides.

As would also be clear to a person skilled in the art, alternatively the esterification could be performed in more than one step, e.g. by first condensing the dicarboxylic acid derivative (IIa) or (IIb) with the alkanolamine (III), and then adding the compound (I) in a next step, followed by addition of (IV). The reactions could take place with or without solvents added. If solvents are present during the reaction, the solvents should be inert to esterification, e.g. toluene or xylene.

The esterification condensation reaction between the components (I), (IIa) or (IIb), (III) and (IV) is suitably effected by heating the mixture at a temperature suitably between 120 and 220° C. for a period of from 2 to 20 hours, optionally at a reduced pressure of from 5 to 200 mbar.

The molar ratio between the compound of structure (I) and the dicarboxylic acid or derivative (IIa) or (IIb) in the reaction mixture is suitably 1:1.2 to 1:10, more preferably 1:1.5 to 1:5, still more preferably 1:2 to 1:4 and most preferably 1:2 to 1:3, the ratio between the compound of structure (I) and alkanolamine (III) is suitably 1:1 to 1:8, more preferably 1:1.2 to 1:6, still more preferably 1:1.5 to 1:5, still more preferably 1:1.5 to 1:4, still more preferably 1:1.5 to 1:3 and most preferably 1:1.5 to 1:2.5, and the ratio between the compound (IV) and the dicarboxylic acid or derivative (IIa) or (IIb) is preferably 1:1 to 1:5, more preferably 1:1.5 to 1:3 and most preferably 1:1.5 to 1:2.

Suitable polyols having 3-4 hydroxyl groups include pentaerythritol, glycerol, trimethylolpropane, di-trimethylolpropane, erythritol and threitol.

Compound (I) and (III) may independently be alkoxylated. The alkoxylation reactions are well-known per se in the art. Generally, for the products of the present invention the following applies. If more than one type of alkylene oxide is reacted with the polyol and/or alkanolamine, the different alkylene oxides may be added in blocks in either order, or may be added randomly. The alkoxylation may be performed by any suitable method known in the art by using e.g. an alkaline catalyst, such as KOH, or an acid catalyst.

The dicarboxylic acid derivative of general formula (IIa) or (IIb) could be a dicarboxylic acid as such, a dicarboxylic acid chloride, a diester of a dicarboxylic acid, or a cyclic anhydride of a dicarboxylic acid. The most suitable derivatives are the dicarboxylic acids and their corresponding cyclic anhydrides. Illustrative examples of dicarboxylic acid derivatives include oxalic acid, malonic acid, succinic acid, glutaric acid, adipic acid, pimelic acid, phthalic acid, tetrahydrophthalic acid, maleic acid, malic acid, tartaric acid, their corresponding acid chlorides, their corresponding methyl or ethyl esters, and their corresponding cyclic anhydrides.

The hydrocarbyl group of the fatty acid having formula (IV) may be linear or branched, saturated or unsaturated. When substituted, the substituents are normally one or more hydroxyl groups. The fatty acid may suitably be tall oil fatty acid, coco fatty acid, tallow fatty acid, soya fatty acid, rape seed fatty acid, myristoleic acid, palmitoleic acid, oleic acid, linoleic acid, α-linolenic acid, arachidonic acid, erucic acid, myristic acid, palmitic acid, stearic acid, arachidic acid, behenic acid, and mixtures thereof. An example of a fatty acid that is substituted is ricinoleic acid, which is substituted by a hydroxyl group in the 12 position. The most preferred fatty acids are unsaturated.

Suitable alkanolamines are N-methyl diethanolamine and N-methyl diisopropanolamine, optionally alkoxylated with ethylene oxide, propylene oxide, butylene oxide or mixtures thereof. If more than one alkylene oxide is reacted with the alkanolamine, the different alkylene oxides may be added in blocks in either order, or may be added randomly.

Also quaternisation is a reaction type that is well-known in the art. For the quaternisation step, the alkylating agents are suitably selected from the group consisting of methyl chloride, methyl bromide, dimethyl sulphate, diethyl sulphate, dimethyl carbonate and benzyl chloride, the preferred alkylating agents being methyl chloride, dimethyl sulphate, dimethyl carbonate or benzyl chloride, and the most preferred methyl chloride. Principally, following an alternative synthesis route, the quaternisation of the alkanolamine could be performed as a first step, which would then be followed by an esterification reaction between (I), (IIa) or (IIb), (IV) and quaternised (III). The quaternisation reaction is normally performed in water or a solvent, such as isopropanol (IPA) or ethanol, or in mixtures thereof, the most preferred solvent being IPA.

The reaction temperature of the quaternising reaction is suitably in the range of from 20 to 100° C., preferably at least 40, more preferably at least 50 and most preferably at least 55° C., and preferably at most 90° C. The heating is preferably stopped when the amount of basic nitrogen is ≤0.1 mmol/g, as measured by titration with 0.1 M perchloric acid in glacial acetic acid.

In a typical reaction the following amounts of the different compounds are used. Per 3 moles of alkanolamine having formula (III), suitably 2-3.5 moles of fatty acid having formula (IV), 1-2 moles of polyol having formula (I) and 3-4 moles of dicarboylic acid or a derivative thereof having formula (IIa) or (IIb) are added.

In another aspect, the invention relates to a method for reverse froth flotation for non-sulfidic ores containing silicate as impurities, especially phosphate ores for the recovery of apatite minerals, in which method the compound or composition described above is used as a collector. In the context of the present invention, the term "non-sulfidic ore" means ores where the value mineral is not in the form of a sulphide, and includes any ore that is conventionally classified as non-sulfidic, inter alia barite, calamine, calcite, magnesite, cassiterite, coal, feldspar, fluorite, glass sand, graphite, heavy metal oxides, iron ores, kaolin clay, phosphate, potash, pyrochlore, scheelite and talc.

For example, by using the collector defined herein in the reverse froth flotation of a phosphate ore, it is possible to achieve an excellent recovery of apatite while keeping the acid insoluble silicate minerals at a very low level.

The effective amount of the collector of the present invention will depend on the amount of impurities present in the pulped phosphate ore and on the desired separation effect, but will in general be in the range of from 100 to 2000 g/ton dry ore, preferably in the range of from 200 to 1500.

In yet another aspect, the present invention relates to a pulp comprising crushed and ground phosphate ore, a mineral collector reagent as defined herein, and optionally a depressant and further flotation aids.

Suitable depressants may be e.g. phosphoric acid, a polysaccharide, alkalized starch, or dextrin.

Further flotation aids that may be present in the froth flotation method are extender oils, and frothers/froth regulators, such as pine oil, MIBC (methylisobutyl carbinol) and alcohols such as hexanol and alcohol ethoxylates/propoxylates.

The present invention is further illustrated by the following examples.

EXAMPLES

Example 1

Synthesis of Collector

Esterification: 42.5 g (0.15 mol) of tall oil fatty acid, 107.2 g (0.9 mol) of methyldiethanolamine, 55.2 g (0.6 mol) of glycerol and 175.3 g (1.2 mol) of adipic acid were charged to a round bottom flask equipped with a condenser, a heating mantel, a stirrer and a nitrogen inlet. The temperature of the reaction mixture was gradually increased during 1 h to 165° C., then vacuum was applied (99 mBar) and the reaction water was distilled off. Then pressure in the flask was gradually decreased till 50 mbar, and the reaction was continued at 166° C. and 50 mbar for approximately 4 h. After that an additional 194.8 g (0.69 mol) of tall oil fatty acid was added, and the reaction was continued at 166° C. and 46-50 mbar for 6 h more. At that time the acid value of the product was 0.35 meq/g. 516.4 g of polyester polyamine were collected.

Quaternisation: 225 g of polyester polyamine and 106 g of isopropanol were added to the autoclave and the reaction mixture was heated up to 60° C. Then 19.6 g of methylchloride was added to the reaction mixture. The postreaction was carried out at 75° C. for 17 h. The total amount of basic nitrogen in the final product was 0.060 meq/g.

The final product was analysed by $^1$H-NMR spectroscopy.
$^1$H-NMR (CD$_3$OD): δ 0.95 (—(CH$_2$)$_n$—$\underline{CH_3}$); δ 1.3 (—CH$_2$—CH=CH—CH$_2$—CH=CH—CH$_2$—($\underline{CH_2}$)$_n$—CH$_3$); δ 1.6 (—O—C(O)—CH$_2$—$\underline{CH_2}$—CH$_2$); δ 2.1(—$\underline{CH_2}$—CH=CH—CH$_2$—CH=CH—$\underline{CH_2}$—(CH$_2$)$_n$—CH$_3$); δ 2.3-2.5 (—O—C(O)—$\underline{CH_2}$—CH$_2$—); δ 2.8(—CH$_2$—CH=CH—$\underline{CH_2}$—CH=CH—CH$_2$—(CH$_2$)$_n$—CH$_3$); δ 3.3 (—CH$_2$—N$^+$(CH$_3$)$_2$—CH$_2$—); δ 3.85 (—$\underline{CH_2}$—N$^+$(CH$_3$)$_2$—$\underline{CH_2}$—); δ 4.1-4.3 (—C(O)—O—$\underline{CH_2}$—CH(OC(O))—$\underline{CH_2}$—O—C(O)—); 4.6 (—C(O)O—$\underline{CH_2}$—CH$_2$—N$^+$(CH$_3$)$_2$—); δ 5.3 (—C(O)—O—CH$_2$—$\underline{CH}$(OC(O))—CH$_2$—O—C(O)—); δ 5.4 (—CH$_2$—$\underline{CH}$=$\underline{CH}$—CH$_2$—CH=CH—CH$_2$—(CH$_2$)$_n$—CH$_3$). By the use of $^1$H, $^{13}$C and 2D NMR techniques the amounts of the components of the obtained composition of the final product were estimated.

Determination of Molecular Weight

A sample of the product was dissolved in tetrahydrofuran and injected on a SEC-system to separate the different homologues from each other. In a SEC system the largest molecules elute first and the smallest molecules elutes last. Fractions were collected and evaporated. They were dissolved in acetonitrile/water 95/5 with 0.5% acetic acid and injected via direct infusion into a QToF MS detector. Different fractions were collected at the following times.

Fraction 1 20.5-25.9 min
Fraction 2 26.0-26.3 min
Fraction 3 26.4-26.7 min
Fraction 4 26.8-27.2 min
Fraction 5 27.3-27.8 min
Fraction 6 27.9-28.6 min
Fraction 7 28.7-29.7 min
Fraction 8 29.8-30.9 min
Fraction 9 31.0-32.5 min
Fraction 10 32.6-34.0 min
Fraction 11 34.1-35.6 min
Fraction 12 35.6-36.5 min The peak at 39.5 minutes is the solvent peak and was therefore not collected for analysis.

The fractions 5-9 were then analyzed on the QToF MS detector.

Analytical Conditions SEC

Precolumn: Phenogel 5µ linear 50×7.8 mm (Phenomenex)
Columns: Phenogel 5µ 300×7.8 mm, three columns in series with pore sizes 500 Å, 100 Å, 50 Å (Phenomenex)
Mobile phase: Tetrahydrofuran
Flow: 0.8 ml/min
Injection volume: 100 µl
Detector: Refractive Index
Analytical Conditions Mass Spectrometer
Direct infusion into Waters Xevo G2 Q-ToF with ESI positive mode
Full Scan Mass Range: 50-4000 m/z Results Based on the results of the MS analysis a number of molecules were identified. In fractions 1-6, molecules containing all four monomers were found in significant amounts. More than 69 area %, based on the chromatogram of FIG. 1 of the product, have components with a molecular weight above 1100. This corresponds to fractions 1-6. For molecules of very similar structure analyzed by refractive index, the detector area % can be approximated to weight %.

Example 2

Flotation Experiments

General Flotation Procedure

Ore Sample:

A phosphate ore of sedimentary origin containing 69% of apatite, 9% of silicates (quartz and feldspar), 21% of calcite and 1% of dolomite was used. The ore sample was deslimed to remove particles with a size less than 40 µm and the remainder had a particle size with $k_{80}$=160 µm.

Flotation Tests:

Flotation tests were performed in a laboratory batch flotation machine with 1.5 l cell. 0.266 kg ore sample was added to the cell, tap water (Stenungsund municipal water with hardness 4° dH) was added to 1.4 l volume, and agitation with 1000 rpm was used throughout the tests. The tests were performed at a pH of 7.8-8.0 (natural) and at ambient temperature, which was about 21° C.

After addition of 700 grams collector per metric ton (g/t) ore sample (the collector was added as a 1% (w/w) aqueous solution), and conditioning for 0.5 minute, air flow was started and froth was withdrawn for three minutes and collected in a stainless bowl. Another 200 g/t portion was then added and after 0.5 minute conditioning, a second froth product was collected for three minutes. After conditioning with further 200 g/t collector, a third froth was collected in the same way.

The froth products and the remaining cell product were dried, weighed and analyzed for content of silicate minerals, defined as insoluble in 25% hydrochloric acid.

The content of acid insoluble remaining in the cell product was then calculated after first, second and third flotation step.

The selectivity factor is defined as the ratio between distribution of "acid insoluble" and distribution of phosphate in the froth (waste). This should be as high as possible.

The collector synthesized in Example 1 was used in the flotation procedure described above, and the flotation results are displayed in Table 1. One can see from the results, that the new collector provides a high selectivity in the reverse flotation of phosphate containing ores.

TABLE 1

| Total dosage of collector (g/t) | Acid insoluble remaining in cell (%) | Acid insoluble in froth (%) | Phosphate recovery (%) | Selectivity factor |
| --- | --- | --- | --- | --- |
| 700 | 6.02 | 83.93 | 99.32 | 52.81 |
| 900 | 2.54 | 83.63 | 98.58 | 52.22 |
| 1100 | 1.52 | 47.79 | 97.43 | 32.94 |

The values in Table 1 are weight percentages.

The invention claimed is:

1. A compound produced by condensation of at least one polyol having 3-4 hydroxyl groups or an alkoxylated product thereof having the formula

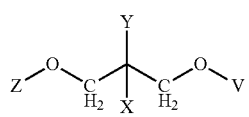

(I)

where Z=—(CH$_2$CH(CH$_3$)O)$_{m1}$(CH$_2$CH$_2$O)$_o$(CH$_2$CH(CH$_3$)O)$_{m2}$T, where T is H, m1 and m2 is independently a number 0-4, and o is 0 or a number from 1 to 10; Y=—CH$_2$OZ, —CH$_2$CH$_3$ or —OZ;
X=H or CH$_2$OZ;
and V=Z or

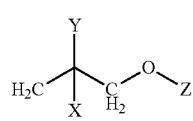

at least one dicarboxylic acid or a derivative thereof having the formula (IIa) or (IIb)

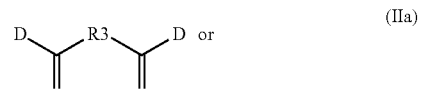

(IIa)

(IIb)

where D is —OH, —Cl, or —OR$^4$, where R$^4$ is a C1-C4 alkyl group; R3 is a bond, an alkylene radical of formula —(CH$_2$)$_z$—, in which z is an integer from 1 to 10, and in which the alkylene radical may be substituted by 1 or 2 —OH groups; the group —CH=CH—, a cycloalkylene, a cycloalkenylene, or an arylene group;

at least one alkanolamine having the formula (III)

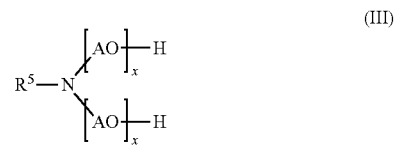

(III)

wherein each x independently is a number between 1 and 5, and the sum of all x on average is a number between 2 and 10, AO is an alkyleneoxy group having 2-4 carbon atoms, R$^5$ is a C1-C4 alkyl group, or [AO]$_x$H; and at least one fatty acid having the formula (IV)

R(C=O)OH (IV)

where R is a hydrocarbyl group having from 7 to 23, carbon atoms, optionally substituted;

followed by reaction with an alkylating agent, suitably a C1-C4 alkyl halide, or dimethyl sulphate, wherein the compound is produced by a process that includes the steps of 1) reacting a mixture comprising the at least one alkanolamine, the at least one fatty acid, the at least one dicarboxylic acid and the at least one polyol having 3-4 hydroxyl groups in the absence of C2-C22 alcohols to form a polyester, and 2) quaternizing the resulting polyester by with the alkylating agent.

2. A compound according to claim 1, where Y is —O(CH$_2$CH(CH$_3$)O)$_{m1}$(CH$_2$CH$_2$O)$_o$(CH$_2$CH(CH$_3$)O)$_{m2}$T, X is H, T is H, and V and Z are both —(CH$_2$CH(CH$_3$)O)$_{m1}$(CH$_2$CH$_2$O)$_o$(CH$_2$CH(CH$_3$)O)$_{m2}$T.

3. A compound according to claim 1 where R$^5$ is a methyl group, A is —CH$_2$CH$_2$— and the sum of all x is 2.

4. A compound according to claim 1, where the alkylating agent is a C1-C4 alkyl halide.

5. A compound according to claim 1 having the structural formula

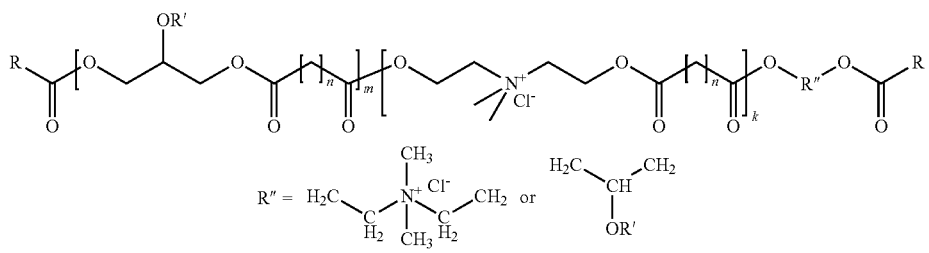

where R is a hydrocarbyl group having from 7 to 23, carbon atoms, optionally substituted; and
R' is H or R(C=O); n is an integer 0-10; m is a number 1-3 and k is a number 2-7.

6. A method for reverse froth flotation for ores containing phosphate or ferruginous minerals containing silicate as impurities, in which method a compound is used as a collector, the compound being produced by condensation of at least one polyol having 3-4 hydroxyl groups or an alkoxylated product thereof having the formula

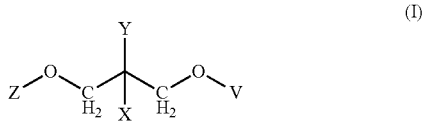
(I)

where Z=—(CH$_2$CH(CH$_3$)O)$_{m1}$(CH$_2$CH$_2$O)$_o$(CH$_2$CH(CH$_3$)O)$_{m2}$T, where T is H, m1 and m2 is independently a number 0-4, and o is 0 or a number from 1 to 10; Y=—CH$_2$OZ, —CH$_2$CH$_3$ or —OZ;
X=H or CH$_2$OZ;
and V=Z or

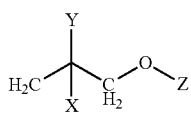

at least one dicarboxylic acid or a derivative thereof having the formula (IIa) or (IIb)

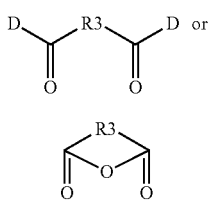
(IIa)

(IIb)

where D is —OH, —Cl, or —OR$^4$, where R$^4$ is a C1-C4 alkyl group; R3 is a bond, an alkylene radical of formula —(CH$_2$)$_z$—, in which z is an integer from 1 to 10, and in which the alkylene radical may be substituted by 1 or 2 —OH groups; the group —CH=CH—, a cycloalkylene, a cycloalkenylene, or an arylene group;

at least one alkanolamine having the formula (III)

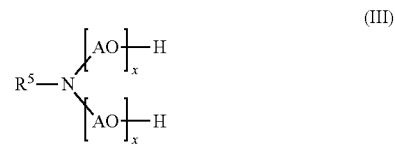
(III)

wherein each x independently is a number between 1 and 5, and the sum of all x on average is a number between 2 and 10, AO is an alkyleneoxy group having 2-4 carbon atoms, R$^5$ is a C1-C4 alkyl group, or [AO]$_x$H; and at least one fatty acid having the formula (IV)

R(C=O)OH (IV)

where R is a hydrocarbyl group having from 7 to 23, carbon atoms, optionally substituted;
followed by reaction with an alkylating agent, suitably a C1-C4 alkyl halide, or dimethyl sulphate wherein the compound is produced by a process that includes the steps of
1) reacting a mixture comprising the at least one alkanolamine, the at least one fatty acid, the at least one dicarboxylic acid and the at least one polyol having 3-4 hydroxyl groups to form a polyester, and
2) quaternizinq the resulting polyester by with the alkylating agent.

7. A method according to claim 6 wherein the ore is a phosphate ore.

8. A method according to claim 7 which comprises the steps of
a) conditioning a pulped phosphate ore, wherein the phosphate ore comprises an apatite mineral or a mixture of such minerals, and gangue minerals, with an effective amount of a silicates collector reagent, which is a compound as defined in claim 1, and optionally other flotation aids and
b) performing a reverse froth flotation process to remove the silicates from the apatite mineral.

9. A pulp comprising a crushed and ground phosphate ore, a compound, and optionally a depressant, wherein the compound is produced by condensation of at least one polyol having 3-4 hydroxyl groups or an alkoxylated product thereof having the formula

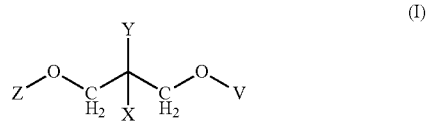
(I)

where Z=—(CH$_2$CH(CH$_3$)O)$_{m1}$(CH$_2$CH$_2$O)$_o$(CH$_2$CH(CH$_3$)O)$_{m2}$T, where T is H, m1 and m2 is independently a number 0-4, and o is 0 or a number from 1 to 10; Y=—CH$_2$OZ, —CH$_2$CH$_3$ or —OZ;

X=H or CH$_2$OZ;

and V=Z or

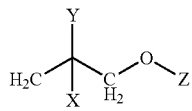

at least one dicarboxylic acid or a derivative thereof having the formula (IIa) or (IIb)

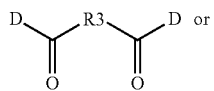 (IIa)

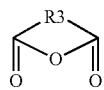 (IIb)

where D is —OH, —Cl, or —OR$^4$, where R$^4$ is a C1-C4 alkyl group; R3 is a bond, an alkylene radical of formula —(CH$_2$)$_z$—, in which z is an integer from 1 to 10, and in which the alkylene radical may be substituted by 1 or 2 —OH groups; the group —CH═CH—, a cycloalkylene, a cycloalkenylene, or an arylene group;

at least one alkanolamine having the formula (III)

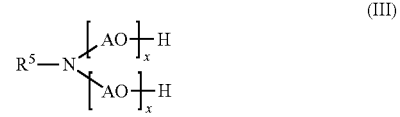 (III)

wherein each x independently is a number between 1 and 5, and the sum of all x on average is a number between 2 and 10, AO is an alkyleneoxy group having 2-4 carbon atoms, R$^5$ is a C1-C4 alkyl group, or [AO]$_x$H; and at least one fatty acid having the formula (IV)

R(C═O)OH (IV)

where R is a hydrocarbyl group having from 7 to 23, carbon atoms, optionally substituted;

followed by reaction with an alkylating agent, suitably a C1-C4 alkyl halide, or dimethyl sulphate wherein the compound is produced by a process that includes the steps of 1) reacting a mixture comprising the at least one alkanolamine, the at least one fatty acid, the at least one dicarboxylic acid and the at least one polyol having 3-4 hydroxyl groups to form a polyester, and
2) quaternizing the resulting polyester by with the alkylating agent.

\* \* \* \* \*